United States Patent [19]
Eykmann et al.

[11] Patent Number: 5,620,423
[45] Date of Patent: Apr. 15, 1997

[54] SYRINGE FOR THE CONTROLLED DISCHARGE OF VISCOUS MATERIALS

[75] Inventors: Rudolf Eykmann, Wehrheim; Joachim Fritze, Friedrichsdorf; Birgit Uhrig, Neu-Anspach; Dieter Schödel, Wiesbaden, all of Germany

[73] Assignee: Heraeus Kulzer GmbH, Germany

[21] Appl. No.: 311,772

[22] Filed: Sep. 23, 1994

[30] Foreign Application Priority Data

Sep. 23, 1993 [DE] Germany .............. 43 32 308.1

[51] Int. Cl.⁶ .............................................. A61M 5/315
[52] U.S. Cl. .................... 604/217; 604/218; 604/232; 604/222
[58] Field of Search .................. 604/208, 218, 604/219, 221, 228, 222, 232, 233, 89–91, 234, 235, 190

[56] References Cited

U.S. PATENT DOCUMENTS

| | | | |
|---|---|---|---|
| 2,902,034 | 9/1959 | Simmonds | 604/222 |
| 3,176,595 | 4/1965 | Schwartz | 604/222 X |
| 3,885,710 | 5/1975 | Cohen | 604/89 X |
| 3,939,833 | 2/1976 | Hansson et al. | 128/218 P |
| 3,998,224 | 12/1976 | Chiquiar-Arias | 604/218 |
| 4,215,701 | 8/1980 | Raitto | 128/763 |
| 4,236,516 | 12/1980 | Nilson | 128/216 |
| 4,266,557 | 5/1981 | Merry | 128/763 |
| 4,615,341 | 10/1986 | Marzoff et al. | 128/765 |
| 4,660,569 | 4/1987 | Etherington | 128/765 |
| 5,377,689 | 1/1995 | Mercereau | 128/763 |
| 5,383,864 | 1/1995 | van den Heuvel | 604/218 |
| 5,496,285 | 3/1996 | Schumacher et al. | 604/218 |

*Primary Examiner*—V. Millin
*Assistant Examiner*—V. Alexander
*Attorney, Agent, or Firm*—Webb Ziesenheim Bruening Logsdon Orkin & Hanson, P.C.

[57] ABSTRACT

A syringe having a stopper configured at least partly as a membrane surface. The stopper is prestressed opposite to the direction of insertion of a rotary piston so that it assumes a stable position at rest. After displacement by the rotary piston, the membrane surface reversibly returns to this stable position after it is depressurized.

12 Claims, 2 Drawing Sheets

SYRINGE FOR THE CONTROLLED DISCHARGE OF VISCOUS MATERIALS

BACKGROUND OF THE INVENTION

1. Field of the Invention

This invention relates to a syringe for the controlled discharge of pasty materials, and, more particularly to a syringe having a plastic cartridge which holds the material and into which, from one end, a rotary piston is inserted.

2. Description of the Prior Art

A syringe of the prior art is described, for example, in the product information published by Heraeus Kulzer GmbH "Charisma—Inlays—Gewinn durch Perfektion und Ästhetik" [Charisma Inlays—Profit from Perfection and Appearance] (31292/D125 sK dt./WPR 12 12 200). These syringes, which contain the viscous dental materials sold under the name "Charisma" (Charisma is a registered trademark of Heraeus Kulzer GmbH), have a cartridge into which the dental material is filled. This cartridge is tapered on its discharge end over its outside circumference in the form of a material discharge nozzle and is closed by attaching a cap. In the end of the cartridge opposite the discharge end, a rotary piston is inserted into a relatively rigid, sleeve-shaped stopper which is in contact with the viscous material contained in the cartridge. The rotary piston is provided with a threaded portion which is guided in a bearing in the form of a nut. To discharge the dental materials from the cartridge, the cap is removed from the cartridge and the rotary piston, which has a handle on one end, is twisted into the cartridge so that the stopper is pushed toward the discharge end of the cartridge and applies pressure to the material. The syringes described above have been used successfully for years.

The cartridges described above which hold the dental materials are generally filled from the rear end, i.e., the end which is opposite the discharge nozzle. After the cartridges are filled from the rear end, the above-mentioned sleeve-shaped stopper is pressed into the open filling end of the cartridge until it is in contact with the filled-in material. Such prior art cartridges which hold the dental material have a slight conicity on the inside, toward the end from which the dental material is filled and the stopper is inserted. This conicity is necessary for removing a workpiece after forming the cartridge by injection molding. Therefore, the stopper is in contact with different tension in the axial direction of the cartridge against the inside wall of the cartridge as it moves from one end of the cartridge to the other. There can be problems with leaks in the cartridge, especially when low-viscosity materials are used. If a stopper is used which has a tighter seal at the transition to the inside wall of the cartridge, during the process of filling the cartridge with material after insertion of the stopper, an air pocket is formed between the material and the stopper and the air pocket cannot escape. To counteract this problem, such stoppers were provided with a hole in the center. A rotary spindle was provided with a mandrel which snapped into the hole to close it. After the material has been discharged from the cartridge and the pressure on the stopper is to be relieved, if the rotary piston is twisted too far out of the syringe, the mandrel can be pulled out of the hole in the stopper thus exposing the material in the cartridge to the atmosphere. This can result in a hardening of the material or a change in the characteristics of the material.

An essential requirement of such syringes is that it must be possible to discharge a precisely controlled amount of the material which is used for the spot to be treated or worked on a tooth or on a dental prosthesis. Moreover, such a syringe is frequently not emptied in a single process but is stored until it is reused. The material inside is thus discharged over several applications. In this case, it is essential that after a discharge of the material from the discharge opening or discharge nozzle of the syringe, no material leaks out. On one hand, such an uncontrolled discharge would thereby interfere with the discharge of the proper amount, and on the other hand, before the discharge nozzle is closed by attaching the cap, no material should adhere to the surfaces which come into contact with the cap. For the reasons indicated above, the rotary piston is usually connected to the stopper so that the rotary piston, as it is being rotated back opposite to the discharge direction, pulls back the stopper and thus relieves the pressure on the material, or an underpressure is created in the cartridge so that no additional material is! discharged from the discharge nozzle. But with this configuration, when the stopper is in very tight contact against the inside wall of the cartridge, the material is pulled back very far into the cartridge, so that the rotary piston must be twisted back into the cartridge very far to resume the discharge of the material from the cartridge. Furthermore, the rotary piston is practically a permanent component of the stopper so that after such a syringe has been used the rotary piston with the stopper cannot be reused.

An object of the present invention is to provide a syringe for the controlled discharge of pasty materials, such as dental materials, so that when a discharge is finished, the syringe performs a controlled depressurization of the material contained in the cartridge and a good seal of the material is achieved by the stopper over the entire length of the cartridge toward the outside, i.e., toward the side of the rotary piston.

SUMMARY OF THE INVENTION

We have developed a syringe in which a disc-shaped portion of the surface of the stopper is configured at least partly as a membrane surface which assumes a stable position in a depressurized state and is prestressed against the direction in which a rotary piston is inserted. After displacement, the membrane surface reversibly returns to this stable position in the depressurized state. The membrane surface is preferably made of plastic. As a result of the membrane surface, the shape, thickness and prestress of which can be precisely specified, it is possible to achieve a controlled depressurization of the dental material when the rotary piston is rotated back out of the cartridge. In one embodiment, the membrane surface is designed so that after the insertion into the cartridge, it is curved or prestressed toward the rotary piston. When the rotary piston is twisted into the cartridge, the end of the rotary piston presses against this curved portion and deforms the membrane surface in the opposite direction toward the material. After a further displacement of the rotary piston, a measured amount of material is discharged in a controlled manner from the discharge opening of the cartridge. Then the rotation of the rotary piston is reversed so that it is pulled back out of the cartridge. A free space between the end of the rotary piston and the membrane surface of the stopper makes it possible for the membrane surface to return to its prestressed initial position in which the curvature points toward the end of the rotary piston.

The stopper is preferably cup-shaped and its base is preferably configured as an elastically deformable surface. In this embodiment, the base or the membrane surface is guided on a ring-shaped part which forms a good contact surface and guide on the inside wall of the cartridge. Such a ring-shaped part has sufficient stability to support the membrane surface on it.

In one simple configuration, the prestress of the membrane surface is achieved by a curvature of the membrane surface opposite to the direction of insertion of the rotary piston. The prestress can be determined by the thickness of the curved portion, i.e., a different thickness of the membrane surface from the middle toward the outside (the membrane surface being thinner in the middle than on its outer edge) and by the elasticity of the material of which the stopper or the membrane surface is made.

A particularly good sealing action between the inside wall of the cartridge and the stopper is achieved by an encircling sealing lip which, in one embodiment, projects downward beyond the base surface, i.e., toward the discharge end of the cartridge, and outward beyond the side walls. In addition, to guarantee the elasticity of the membrane surface toward its outer edge, there is an at least partly encircling, but preferably completely encircling, groove on the inside of the cup-shaped stopper in the transitional area between the wall of the cup and the base of the cup. This groove forms a design bending point of the membrane surface in the transitional area between the membrane and the side wall of the cup-shaped stopper. This groove also forms a sufficient free space which is completely closed during the movement of the membrane surface into its stable, prestressed position. The encircling sealing lip, which projects downward beyond the base of the cup-shaped stopper and outward beyond the side wall of the cup-shaped stopper, can, if it is configured with an appropriate length, be bent toward the axis of the cartridge as a result of its contact with the wall of the cartridge so that a bending moment is exerted on the membrane surface and so that the membrane surface is prestressed inward toward the end of the rotary piston. Such a configuration of the stopper also has the particular advantage that the prestress of the membrane surface originates only when the stopper is inserted into the cartridge, and even after a rather long storage of the stopper after manufacturing and before it is inserted into a syringe, the stopper and its membrane surface still exhibit sufficient prestress.

In addition to the one sealing lip which projects beyond the base of the cup, additional channels and/or grooves can be formed in the outside of the side walls of the cup-shaped stopper, where remaining webs between the channels form individual sealing and guide areas.

The stopper itself and its side wall can have a conical shape, where the diameter of the side wall increases toward a free end. In one such configuration of the stopper, there is an additional guiding and contact surface formed on the rear portion of the stopper as a result of the enlarged diameter, which is in tight contact against the inside wall of the cartridge.

The stopper can be inserted into the cartridge so that after the cartridge is loaded, the cartridge can be closed in a sealed manner on one end and so after it has been filled, no additional caps need to be applied to this end of the cartridge even if the cartridge is to be placed in storage for a period of time.

The rotary piston should have a curved end, and particular preference is given to a rounding of the end of the rotary piston which equals the maximum travel of the base surface of the stopper in the forward direction of the rotary piston. Even with high-viscosity materials, there is no damage to the membrane surface since even when a large force is applied, it is in contact with the curved portion of the end of the rotary piston.

In an additional configuration of the syringe, the cartridge, on its inside surface and in particular on the end at which the rotary piston is inserted into the cartridge, has a stop against which the stopper can come in contact when the cartridge is filled from the discharge end. This stop can be formed, for example, by a step-wise reduction of the inside diameter of the cartridge.

The membrane surface of the stopper preferably has a thickness between 0.2 and 0.6 mm, with a preferred thickness of approximately 0.4 mm in the middle of the membrane surface. The encircling sealing lip which projects downward beyond the base surface of the stopper, by means of which the indicated moment is exerted on the membrane surface, preferably projects approximately 0.5 to 1 mm beyond the base surface. The recess or the radius which is located on the inside in the transitional region between the base surface and the side wall of the stopper is approximately 0.5 mm, with a depth of approximately 0.2 to 0.3 mm.

Additional details and features of the invention are explained in greater detail in the following description of the invention which is illustrated in the accompanying drawings.

DESCRIPTION OF THE PREFERRED EMBODIMENTS

Figure 1:
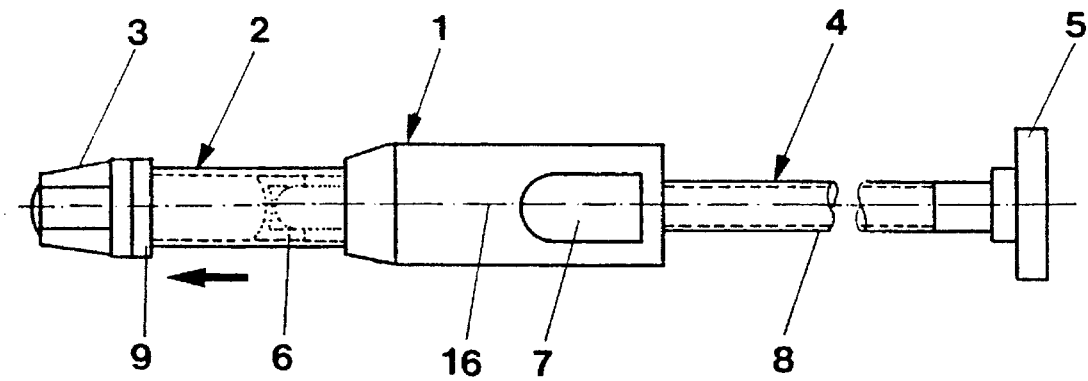
FIG. 1 is a lateral plan view of one embodiment of a syringe with an adapter and a cartridge inserted therein in accordance with the present invention.

A syringe for the controlled discharge of viscous materials as shown in FIG. 1 has an adapter 1, in which cartridge 2 is held and which is closed by a cap 3 on a free end projecting out of the adapter 1. The cartridge 2 is filled with a material to be discharged. A threaded portion or rotary piston 4 which has a handle 5 on a free end is inserted into the adapter 1 on an end opposite the cartridge 2. The inserted end of the rotary piston 4 presses against a stopper 6 in the cartridge 2, which is indicated by broken lines in FIG. 1. The rotary piston 4 is held in the adapter part 1 in a bearing 7 in which it is guided by means of a threaded portion 8. To discharge material from the cartridge 2 via the discharge nozzle 9, as shown in the embodiments in FIGS. 2 and 3, the rotary piston 4 is twisted at the handle 5 so that the stopper 6 is advanced in the direction indicated by the arrow in FIG. 1 and presses against the material contained in the cartridge 2. After use, the stopper 6 is depressurized by twisting back the rotary piston 4 and releasing the connection between the rotary piston 4 and the stopper 6 and then replacing the cap 3 on the discharge nozzle 9.

Figure 2:
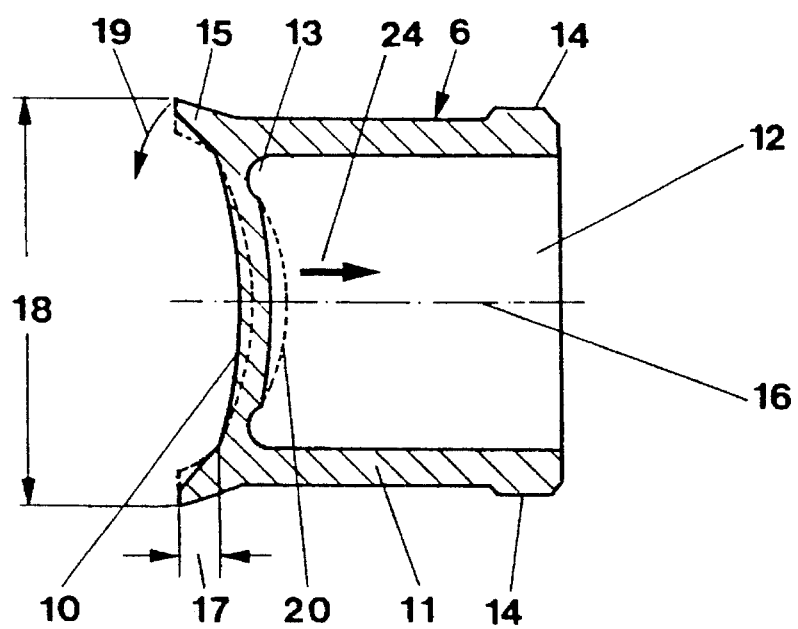
FIG. 2 is a sectional view of the stopper of the syringe shown in FIG. 1 along an axis of the cartridge.
Figure 3:
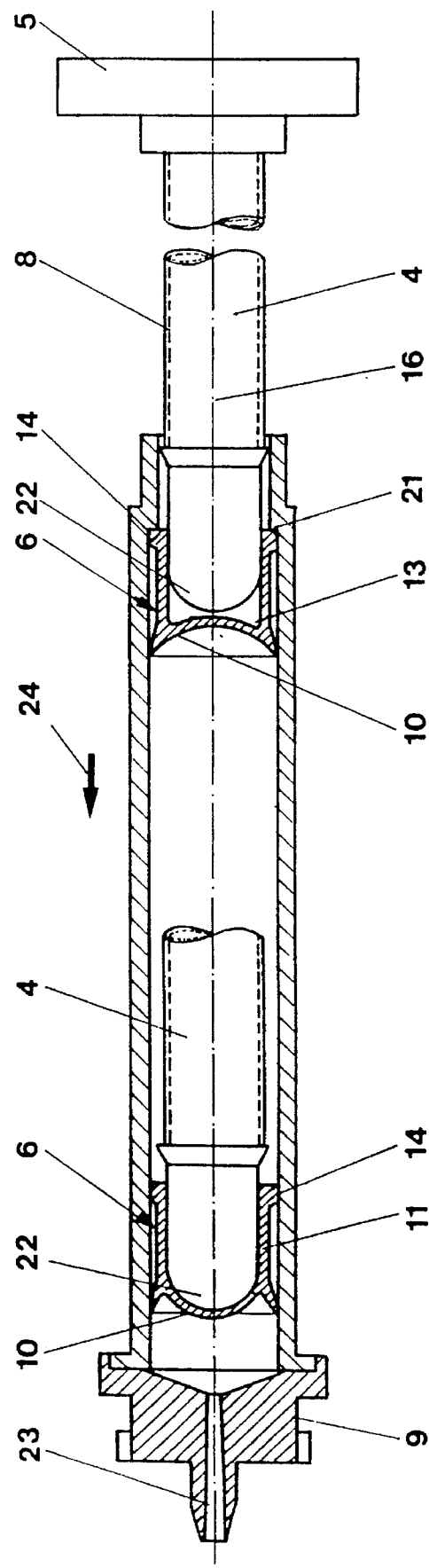
FIG. 3 is a cross section through the cartridge of the syringe shown in FIG. 1, with two different positions of the stopper in the cartridge, on one hand in a position displaced toward the forward discharge end, and on the other hand in a rear, retracted position.

The stopper 6, which is shown in an enlarged section in FIG. 2, is designed in the form of a cup-shaped part with a cup base 10 which forms a membrane surface, and side wall 11. The cup base or the membrane surface 10 is prestressed toward the open side 12 of the stopper 6, i.e., it is curved in a convex manner. The radius of curvature of the membrane surface 10 in the stable position illustrated in FIG. 2 in which it is not inserted in the cartridge 2, is approximately 100 to 150 mm. In the transitional area between the cup base or membrane surface 10 and the side wall 11, an encircling groove 13 is formed with a radius of approximately 0.5 mm and a depth, starting from the inside of the membrane surface 10, of approximately 0.2 mm. On the upper end of the side wall 11, a web 14 runs around the outside and forms a contact or guide surface against the inside wall of the cartridge 2, as shown in FIG. 3. Instead of this web, the outside diameter of the stopper 6 can also be increased on this end, so that the side wall 11 is conical. On the other end of the side wall 11, an encircling sealing lip 15, seen in the direction of the axis 16 of the stopper, projects both beyond the underside of the membrane surface 10 and also radially outward beyond the side wall 11. The sealing lip 15 projects radially by approximately 0.5 mm and projects beyond the underside of the membrane surface 10, as indicated by the distance 17 in FIG. 2, by approximately 1 to 1.5 mm. The diameter 18 of the stopper 6 on the end of the encircling sealing lip 15 is approximately 1 mm larger than the inside diameter of the cartridge 2. When the stopper 6 is inserted into the cartridge 2, the encircling sealing lip 15 is pressed radially inward in the direction indicated by the arrow 19 thereby exerting a moment on the membrane surface 10 so that its curvature is increased toward the inside of the cup-shaped stopper 6, as indicated by the broken line 20 in FIG. 2. On one hand, this prestress causes a large travel of the membrane surface 10 toward the rotary piston 4 and on the other hand, a force is exerted on the encircling sealing lip 15 by means of the membrane surface 10 toward the inside, wall of the cartridge 2, thereby increasing the sealing action of the sealing lip against the inside wall of the cartridge 2.

The right side of FIG. 3, which shows the stopper 6 displaced toward the right, illustrates the position in which the stopper 6 is displaced after a cartridge 2 has been filled with viscous dental material. In this position, the stopper 6 comes into contact with the free end surface of its side wall 11 against a shoulder 21. Starting from this position, the rotary piston 4, which has a rounded end 22 having a radius which preferably corresponds to one-half the diameter of the rotary piston 4, is displaced by rotation around the axis 16 in the direction indicated by the arrow 24. As a result of this displacement, the membrane surface 10 is curved in the opposite direction, as illustrated in the position of the stopper 6 on the left side of FIG. 3. The base surface 10 is curved to correspond to the rounded portion of the end 22 of the rotary piston 4, so that even if a large force is applied, there is no damage to the membrane surface 10. In this position in which the membrane surface 10 is in contact with the end 22 of the rotary piston 4, a moment is exerted on the encircling sealing lip 15 which is pressed radially outward with respect to the axis 16 against the inside wall of the cartridge 2. After the desired quantity of material has been discharged from the cartridge 2 via the discharge opening 23, the rotary piston 4 is turned in the opposite direction, and thus the pressure is removed from the membrane surface 10. The base of the cup or the membrane surface 10 then returns to its initial prestressed position, which is illustrated on the right-hand side in FIG. 3. As the membrane surface 10 is returning to its initial position, an underpressure is generated in the cartridge 2 which acts on the material and pulls the material which is still in the discharge opening 23 of the discharge nozzle 9 back into the cartridge 2. Consequently, there is no running or dripping of the material.

The syringe or cartridge 2 which is closed by the stopper 6 has the advantage that it can be filled with material by the manufacturer from the front, i.e., from the discharge end of the cartridge 2. First, the stopper 6 is inserted into the empty cartridge 2, with which it is in tight contact by means of the encircling sealing lip 15 against the inside wall of the cartridge 2. Then, the cartridge is placed in a charging station and the material is injected into the cartridge 2, where the stopper 6 is displaced toward the rear end of the cartridge in the direction indicated by the arrow 25 in FIG. 2 until the stopper 6 comes in contact with the shoulder 21. During this filling process, no air pockets are formed in the vicinity of the stopper 6 since any air which is in front of the stopper is discharged from the cartridge 2 in the initial phase of the process of filling the cartridge with material. Then the filled cartridge 2 is closed. During the process of filling the cartridge 2, the pressure on the encircling sealing lip 15 is relieved by the material pressing on the base surface 10 of the stopper 6 so that the stopper 6 can move very easily along the inside wall of the cartridge 2.

The stopper 6 is preferably made of polyethylene, which has the major advantage that on one hand it is sufficiently flexible and on the other hand has sufficient strength, even at points where the structure is thin.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and any and all equivalents thereof.

What is claimed is:

1. A syringe for the controlled discharge of a pasty material, comprising: a cartridge for holding the material; a cup-shaped stopper having an open end and having a base surface configured as an elastically deformable disc-shaped membrane surface; and a rotary piston having an inserted end, with the rotary piston configured to be inserted into one end of the cartridge, with the rotary piston, on the inserted end, pressing against the membrane surface, with the stopper having an exterior configuration which tightly closes an inside cross section of the cartridge, and with the membrane surface of the stopper configured as a plastic membrane surface which, in a depressurized state, is prestressed and assumes a stable position with respect to a longitudinal insertion direction of the rotary piston, so that after a displacement of the membrane surface by the rotary piston, the disc-shaped membrane surface returns reversibly to the stable position in the depressurized state, wherein the membrane surface in the depressurized state is configured as a curvature, wherein a concavity of the curvature faces in a direction opposite to the longitudinal direction of insertion of the rotary piston, wherein the cartridge includes an inside wall and the stopper includes a sealing lip in contact with the inside wall of the cartridge, wherein the sealing lip is configured in an encircling manner, wherein the sealing lip includes an outer end which, prior to insertion into the cartridge, has a diameter larger than an inside diameter of the cartridge, wherein the stopper includes a side wall, wherein the sealing lip projects downward beyond the prestressed membrane surface and outward beyond the side wall, and wherein the sealing lip, which is in contact under tension against the inside wall of the cartridge, exerts a bending moment on the membrane surface which is directed opposite to the longitudinal direction of insertion of the rotary piston.

2. A syringe as claimed in claim 1, wherein the side wall of the cup-shaped stopper, in a transitional region between the open end of the stopper and the membrane surface, forms an at least partly encircling groove.

3. A syringe as claimed in claim 2, wherein the encircling groove has a radius of approximately 0.5 mm.

4. A syringe as claimed in claim 1, wherein a diameter of the side wall of the stopper increases toward the open end.

5. A syringe as claimed in claim 1, wherein the inserted end of the rotary piston is curved.

6. A syringe as claimed in claim 5, wherein the curvature of the inserted end of the rotary piston is configured as a function of the maximum travel of the membrane surface of the stopper in a direction of forward motion of the rotary piston.

7. A syringe as claimed in claim 1, wherein the cartridge forms a tight seal for the material on one side.

8. A syringe as claimed in claim 1, wherein the cartridge includes an inside shoulder, and wherein the stopper, when adjacent an insertion end of the rotary piston, is configured to contact the shoulder formed on the inside of the cartridge.

9. A syringe as claimed in claim 1, wherein the membrane area has a thickness between 0.2 and 0.6 mm.

10. A syringe as claimed in claim 1, wherein the encircling sealing lip projects outward by a distance in the range of 0.2 to 0.7 mm beyond the side wall.

11. A syringe as claimed in claim 1, wherein the encircling sealing lip projects downward by a distance in the range of 0.3 to 0.5 mm beyond the membrane surface in the depressurized state.

12. A syringe as claimed in claim 1, further including a radially-encircling projection on an outside of the stopper side wall.

* * * * *